(12) United States Patent
Takashino et al.

(10) Patent No.: US 9,827,034 B2
(45) Date of Patent: Nov. 28, 2017

(54) TREATMENT DEVICE AND TREATMENT SYSTEM

(71) Applicant: OLYMPUS CORPORATION, Tokyo (JP)

(72) Inventors: Tomoyuki Takashino, Fuchu (JP); Yusuke Takei, Hino (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/051,229

(22) Filed: Feb. 23, 2016

(65) Prior Publication Data
US 2016/0166307 A1   Jun. 16, 2016

Related U.S. Application Data

(63) Continuation of application No. PCT/JP2014/084363, filed on Dec. 25, 2014.
(Continued)

(51) Int. Cl.
*A61B 18/14* (2006.01)
*A61B 18/08* (2006.01)
(Continued)

(52) U.S. Cl.
CPC ........ *A61B 18/085* (2013.01); *A61B 18/1445* (2013.01); *A61B 2017/00115* (2013.01);
(Continued)

(58) Field of Classification Search
CPC .... A61B 2018/2825; A61B 2018/2926; A61B 17/282; A61B 18/1442; A61B 2018/00791; A61B 2018/1455
See application file for complete search history.

(56) References Cited

U.S. PATENT DOCUMENTS 5,876,401 A * 3/1999 Schulze ........... A61B 17/07207
                                                    606/41
8,382,754 B2 * 2/2013 Odom ................ A61B 18/1445
                                                    606/207
(Continued)

FOREIGN PATENT DOCUMENTS

EP        1707143       10/2006
EP        2604210        6/2013
(Continued)

OTHER PUBLICATIONS

Jul. 7, 2016 International Preliminary Report on Patentability issued in International Application No. PCT/JP2014/084363.
(Continued)

*Primary Examiner* — Ronald Hupczey, Jr.
(74) *Attorney, Agent, or Firm* — Oliff PLC

(57) ABSTRACT

A treatment device includes: a treatment portion including an abutment surface which is abutted on the living body tissue, and a back surface opposed to the abutment surface, the treatment portion being capable of applying energy to the living body tissue via the abutment surface, and heat being transferred toward the back surface in accordance with the application of the energy; a cover covering the back surface of the treatment portion; and an adjuster disposed between the treatment portion and the cover, and configured to vary a distance between the treatment portion and the cover, and to adjust an air layer region between the treatment portion and the cover.

7 Claims, 11 Drawing Sheets

Related U.S. Application Data

(60) Provisional application No. 61/921,269, filed on Dec. 27, 2013.

(51) Int. Cl.
*A61B 17/00* (2006.01)
*A61B 18/00* (2006.01)
*A61B 90/00* (2016.01)

(52) U.S. Cl.
CPC .............. *A61B 2018/0063* (2013.01); *A61B 2018/00101* (2013.01); *A61B 2018/00601* (2013.01); *A61B 2018/00791* (2013.01); *A61B 2018/00898* (2013.01); *A61B 2090/061* (2016.02)

(56) References Cited

U.S. PATENT DOCUMENTS

| | | |
|---|---|---|
| 2006/0224158 A1 | 10/2006 | Odom et al. |
| 2011/0319886 A1* | 12/2011 | Chojin .............. A61B 18/1445 606/37 |
| 2013/0150842 A1 | 6/2013 | Nau, Jr. et al. |
| 2014/0276805 A1 | 9/2014 | Sobajima et al. |

FOREIGN PATENT DOCUMENTS

| | | |
|---|---|---|
| JP | 2005-137679 A | 6/2005 |
| JP | 2005-261916 A | 9/2005 |
| WO | 2013/180293 A1 | 12/2013 |

OTHER PUBLICATIONS

Mar. 24, 2015 Search Report issued in International Patent Application No. PCT/JP2014/084363.

Jul. 25, 2017 Search Report issued in European Patent Application No. 14873779.4.

\* cited by examiner

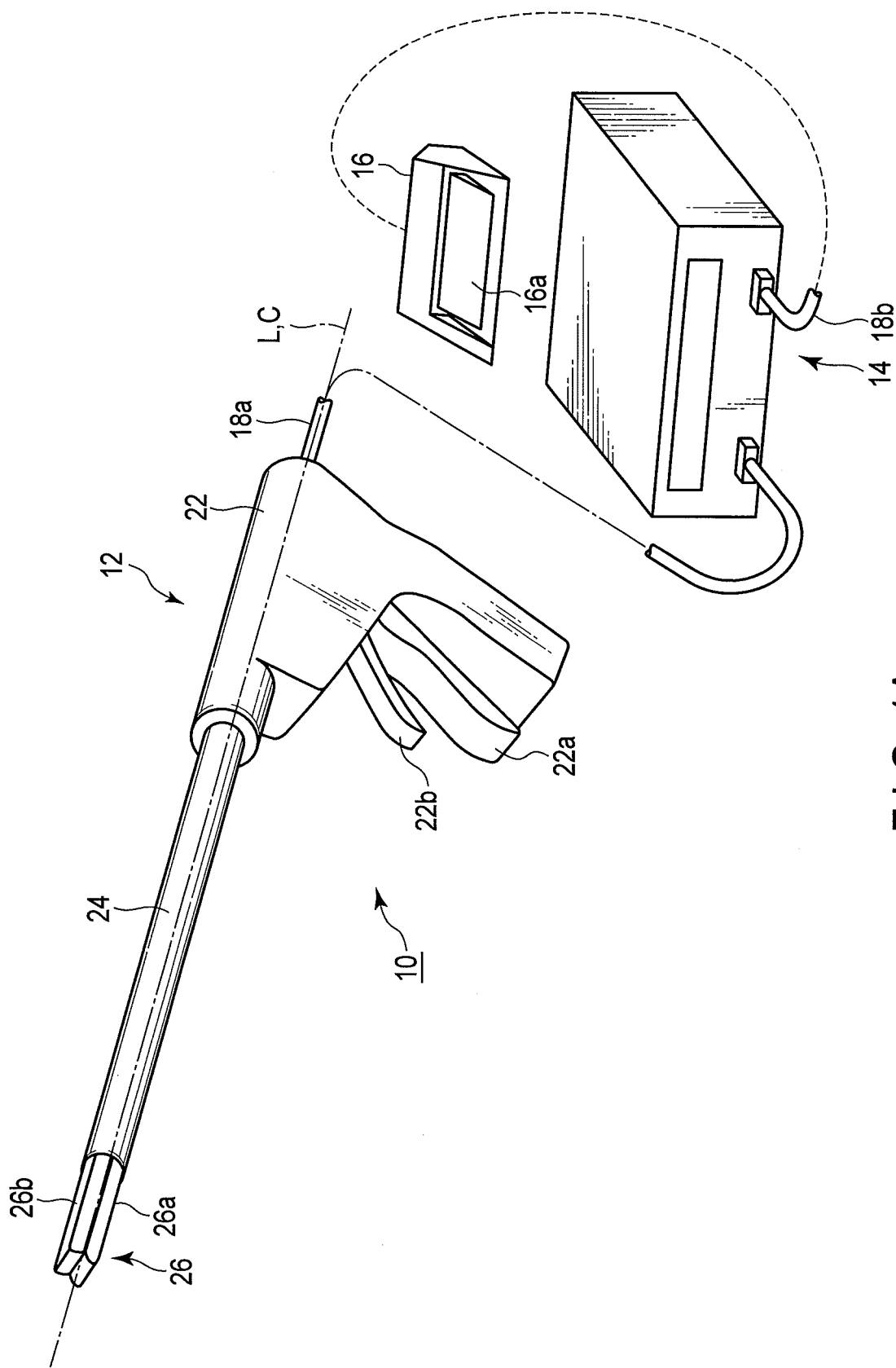
F I G. 1A

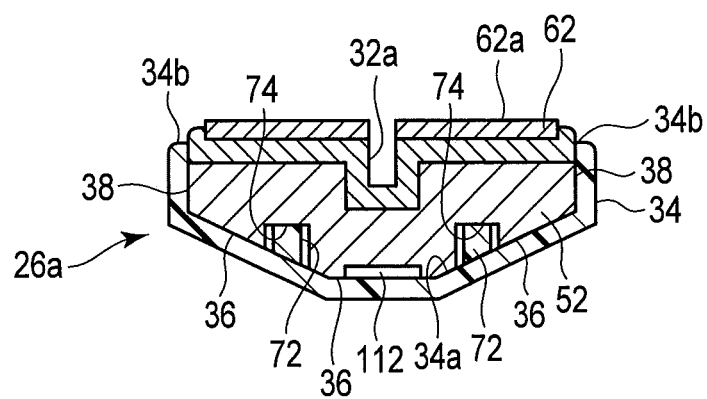
F I G. 7A
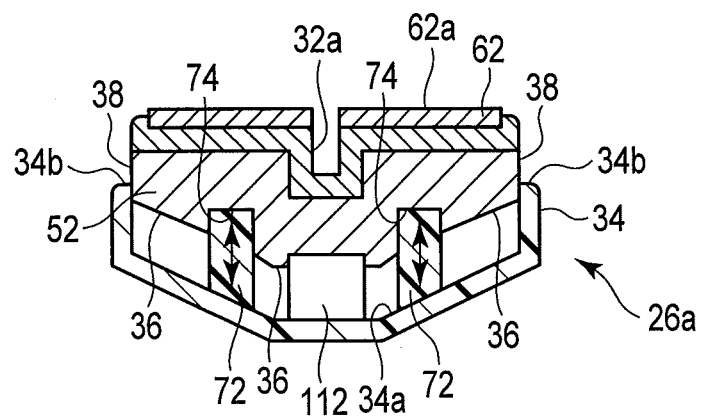
F I G. 7B

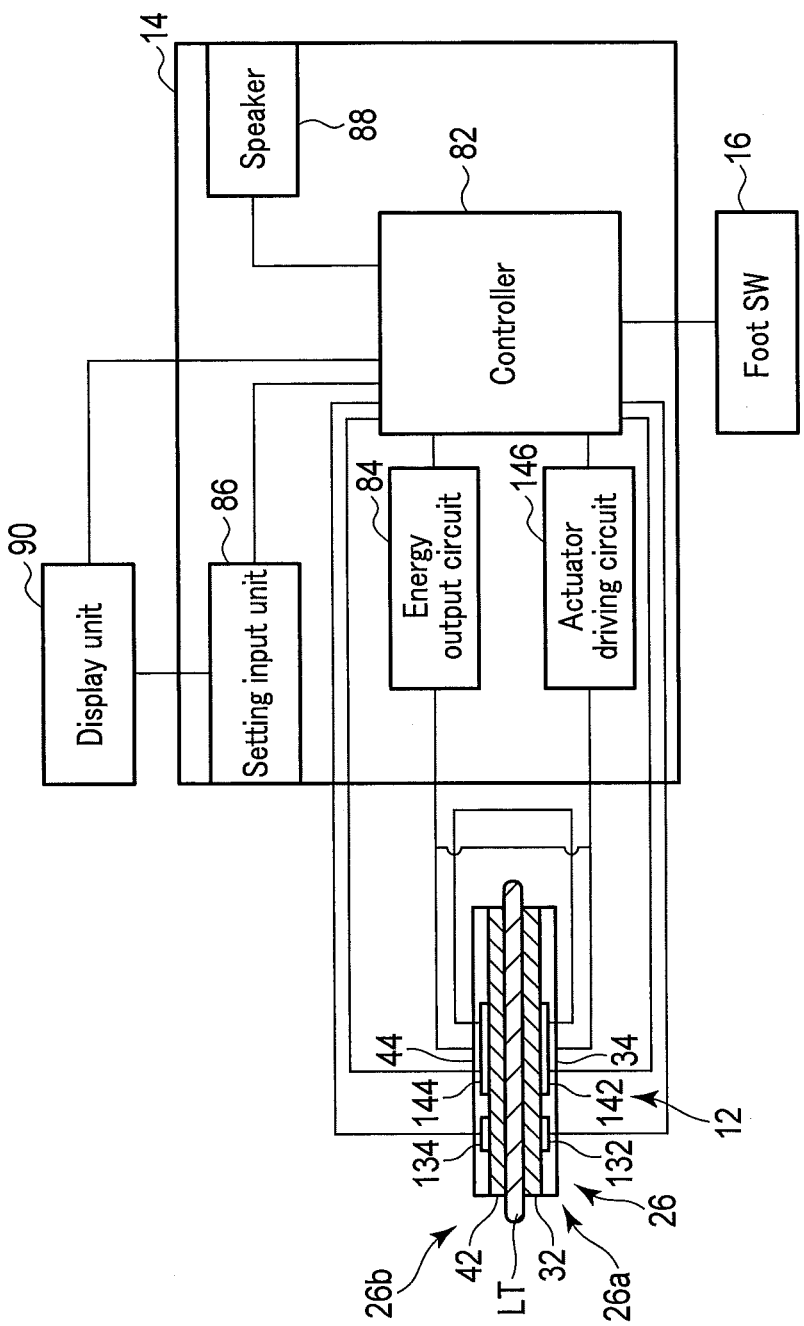
F I G. 8

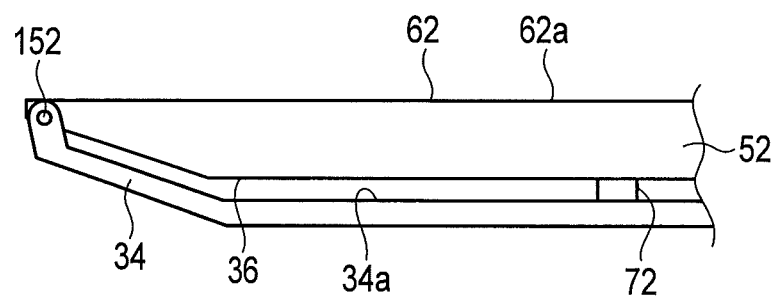
F I G. 10A
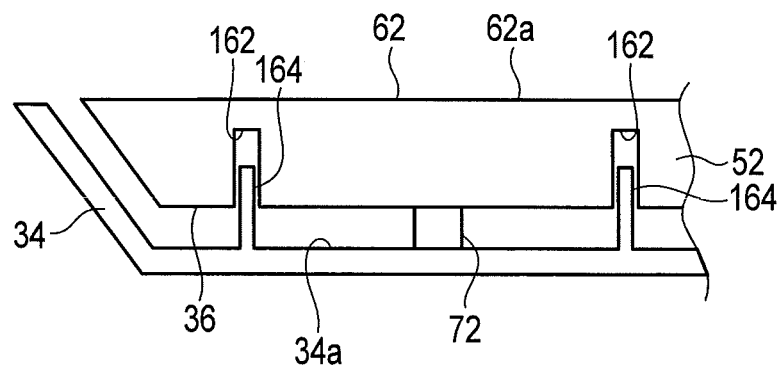
F I G. 10B

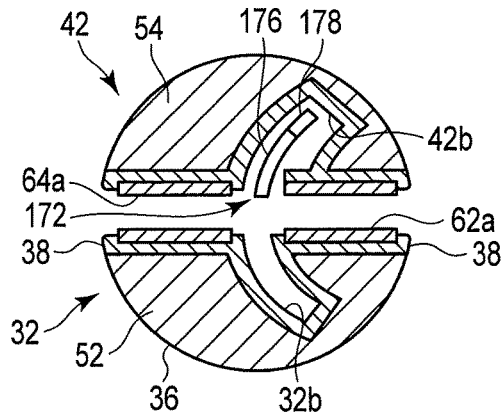
F I G. 11A
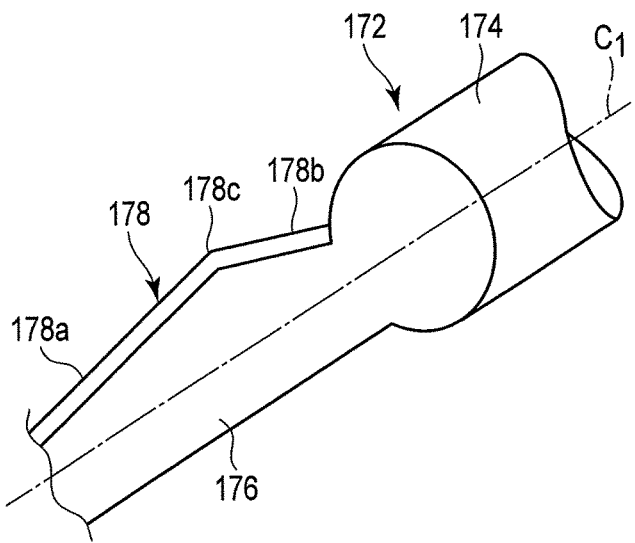
F I G. 11B
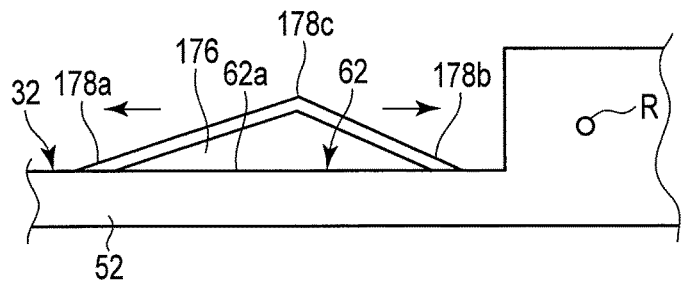
F I G. 11C

TREATMENT DEVICE AND TREATMENT SYSTEM

CROSS-REFERENCE TO RELATED APPLICATIONS

This application is a Continuation Application of PCT Application No. PCT/JP2014/084363, filed Dec. 25, 2014 and based upon and claiming the benefit of U.S. Provisional Application No. 61/921,269, filed Dec. 27, 2013, the entire contents of which are incorporated herein by reference.

BACKGROUND OF THE INVENTION

1. Field of the Invention

The present invention relates to a treatment device and a treatment system for use in treating a living body tissue.

2. Description of the Related Art

For example, Jpn. Pat. Appln. KOKAI Publication No. 2005-137679 discloses a treatment body of a treatment device for use in treating a living body tissue. In this treatment body, an air layer is formed as a thermal insulation layer between a treatment portion and a cover of a back surface of the treatment portion.

BRIEF SUMMARY OF THE INVENTION

According to one aspect of the present invention, a treatment device which is capable of treating a living body tissue by using energy, includes: a treatment portion including an abutment surface which is abutted on the living body tissue, and a back surface opposed to the abutment surface, the treatment portion being capable of applying energy to the living body tissue via the abutment surface, and heat being transferred toward the back surface in accordance with the application of the energy; a cover covering the back surface of the treatment portion; and an adjuster disposed between the treatment portion and the cover, and configured to vary a distance between the treatment portion and the cover, and to adjust an air layer region between the treatment portion and the cover.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic perspective view illustrating a treatment system according to a first embodiment.

FIG. 7A is a schematic transverse cross-sectional view illustrating a first holding section of an end effector of a treatment device of the treatment system according to the second embodiment, and illustrating a state in which an inner surface of a cover abuts on a back surface of a treatment portion.

FIG. 7B is a schematic transverse cross-sectional view illustrating the first holding section of the end effector of the treatment device of the treatment system according to the second embodiment, and illustrating a state in which the inner surface of the cover is spaced apart from the back surface of the treatment portion.

FIG. 8 is a schematic block diagram of a treatment system according to a third embodiment.

FIG. 10A is a schematic longitudinal cross-sectional view illustrating a first holding section of an end effector of a treatment device of a treatment system according to a fourth embodiment.

FIG. 10B is a schematic longitudinal cross-sectional view illustrating a first holding section of an end effector of a treatment device of a treatment system according to a modification of the fourth embodiment shown in FIG. 10A.

FIG. 11A is a schematic transverse cross-sectional view illustrating an end effector of a treatment device of a treatment system according to a fifth embodiment.

FIG. 11B is a schematic perspective view illustrating a cutter unit which is disposed in the end effector of the treatment device of the treatment system according to the fifth embodiment.

FIG. 11C is a schematic side view illustrating a state in which a blade of the cutter unit, which is disposed in the end effector of the treatment device of the treatment system according to the fifth embodiment, is projected toward a first treatment portion.

DETAILED DESCRIPTION OF THE INVENTION

Figure 1B:
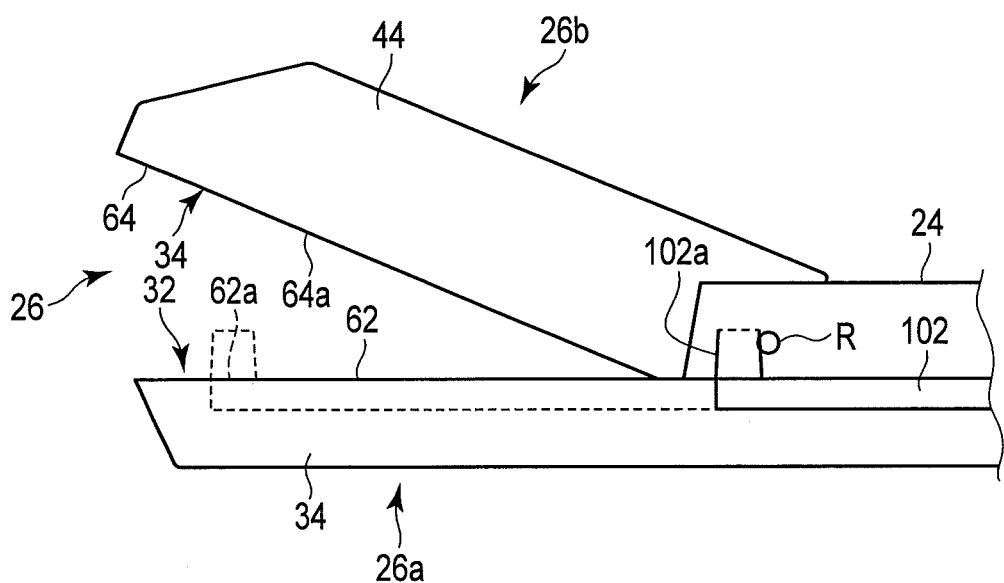
FIG. 1B is a schematic view illustrating an end effector of a treatment device of the treatment system according to the first embodiment.
Figure 2:
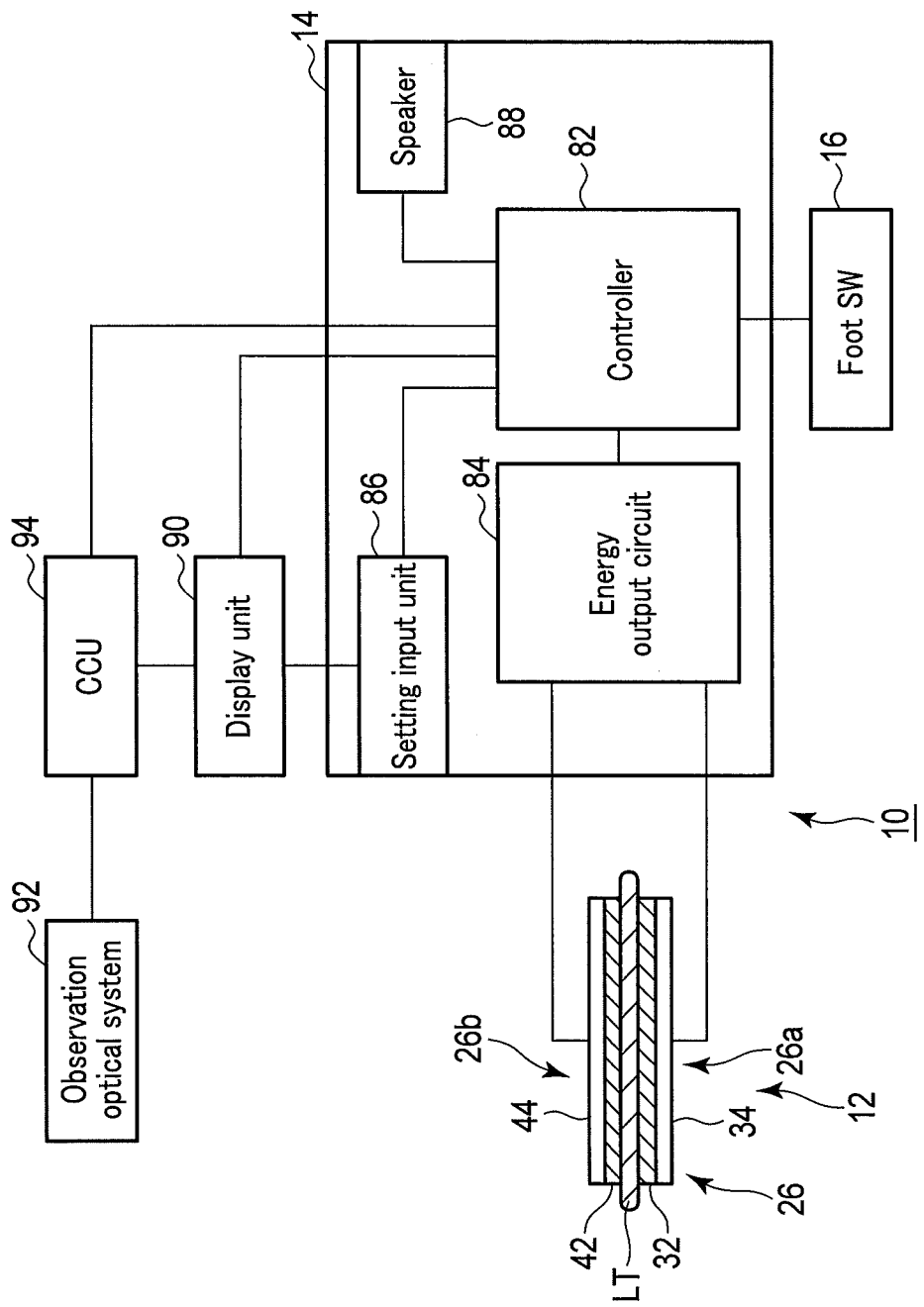
FIG. 2 is a schematic block diagram of the treatment system according to the first embodiment.

Embodiments of the present invention will be described hereinafter with reference to the accompanying drawings.

A first embodiment is described with reference to FIG. 1A to FIG. 5.

As illustrated in FIG. 1A, a treatment system 10 according to this embodiment includes an energy treatment device (therapeutic treatment device) 12 which can treat a living body tissue, and an energy source (controller) 14. Here, as the energy treatment device 12, a linear-type surgical treatment device for performing treatment, for example, through an abdominal wall, is described by way of example. A foot switch (which may be a hand switch) 16 including a pedal 16a is connected to the energy source 14 by a cable 18b. In the meantime, the treatment device 12 and energy source 14 are connected by a cable 18a.

The energy treatment device 12 includes a handle 22 which is supported by an operator, a shaft 24 which extends from the handle 22 along a center axis C (longitudinal axis L), and an end effector (treatment body) 26. In this embodiment, a surgeon operates the pedal 16a of the foot switch 16, thereby switching ON/OFF of supply of energy from an energy output circuit 84 (to be described later) of the energy source 14 shown in FIG. 2 to the end effector 26 (specifically, first and second energy output portions 62, 64 to be described later) of the treatment device 12. While the pedal 16a is being pressed, energy is output from the energy source 14, based on a state in which the energy source 14 is properly set by a setting input unit 86 (to be described later) (a state in which an energy output amount, an energy output timing, etc. are controlled). If the pressing of the pedal 16a is released, the output of energy is forcibly stopped.

As illustrated in FIG. 1A, the handle 22 includes an operation lever (operation portion) 22a which operates first and second treatment portions 32 and 42 (to be described later) such that the first and second treatment portions 32 and 42 may open/close relative to each other. The end effector 26 is disposed at a distal end of the shaft 24. As illustrated in FIG. 1A and FIG. 1B, the end effector (treatment body of a living body tissue of a treatment target) 26 includes a first holding section 26a and a second holding section 26b. By the operation of the operation lever 22a of the handle 22, the first and second holding sections 26a and 26b rotate relative to each other about a rotational axis R (see FIG. 1B) by a publicly known mechanism, thus being able to move closer to or away from each other.

The first holding section 26a includes the first treatment portion 32 and a first cover 34. The second holding section 26b includes the second treatment portion 42 and a second cover 44.

As illustrated in FIG. 3A to FIG. 5, the first and second treatment portions 32 and 42 include a pair of jaws (first and second jaws) 52 and 54 that are openable/closable relative to each other, which are operated by the operation lever 22a, and the first and second energy output portions 62 and 64.

In the meantime, although the structure of the end effector 26 is described here by taking the first holding section 26a as an example, it is preferable that the second holding section 26b has the same structure. Specifically, a description of the detailed configuration of the second holding section 26b is omitted.

The first holding section 26a includes the first jaw 52, the first energy output portion 62 having a first holding surface (abutment surface that is abutted on a living body tissue) 62a, and the first cover 34 which is disposed on a back surface 36 of the first jaw 52. The first jaw 52 and first energy output portion 62 constitute the first treatment portion 32. The first holding section 26a includes an adjuster 72 between itself and the first cover 34 that is disposed on the back surface 36 of the first jaw 52. The adjuster 72 couples the treatment portion 32 and cover 34. The cover 34 includes an inner surface 34a which is opposed to the back surface 36 of the treatment portion 32 and can come in contact with or approach, and can move away from, the back surface 36 of the treatment portion 32, and an edge portion 34b which can approach, and move away from, the holding surface 62a.

The first jaw 52 is formed of, for example, stainless steel or the like. The first cover 34 is formed by using a material having a low coefficient of thermal conductivity, heat resistance, and adiathermancy for preventing a thermal effect on a living body tissue around the living body tissue of the treatment target. The first cover 34 is formed by using, for example, an engineering plastic, such as PEEK, ABS resin or polycarbonate.

The first energy output portion 62 is provided on the first jaw 52, and the holding surface 62a of the first energy output portion 62 is opposed to the second holding section 26b. It is preferable that the jaw 52 has an insulation property as a whole. For example, a high-frequency electrode or a heater is used for the first energy output portion 62, and the first energy output portion 62 is connected to the energy source 14. Thus, energy is applied via the holding surface (abutment surface) 62a to the living body tissue that is in contact with the holding surface 62a of the first energy output portion 62, and the living body tissue is treated by heat energy. In addition, the first jaw 52 conveys heat to the back surface 36 in accordance with application of energy.

Figure 3A:
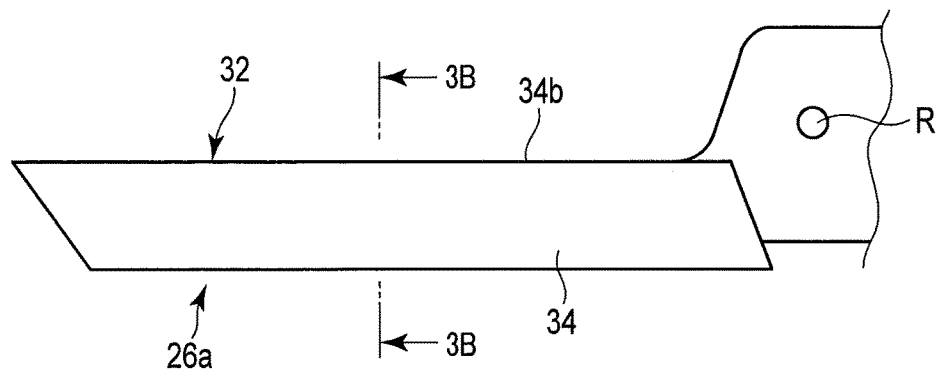
FIG. 3A is a schematic side view illustrating a first holding section of the end effector of the treatment device of the treatment system according to the first embodiment, and illustrating a state in which an inner surface of a cover abuts on a back surface of a treatment portion.
Figure 3B:
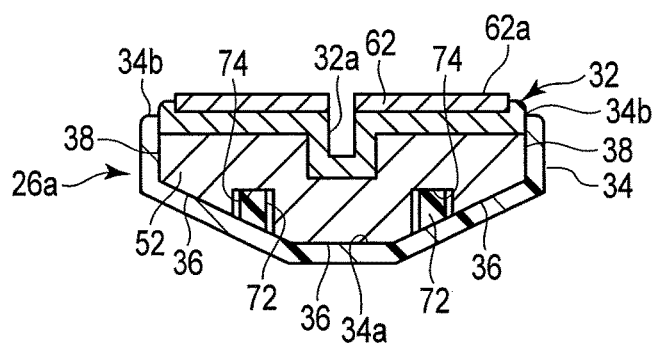
FIG. 3B is a schematic transverse cross-sectional view, taken along line 3B-3B in FIG. 3A, illustrating the first holding section of the end effector of the treatment device of the treatment system according to the first embodiment.
Figure 4A:
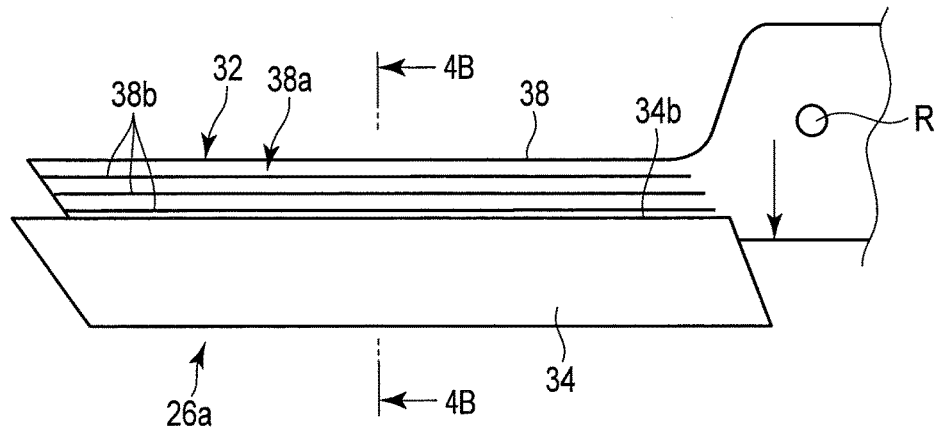
FIG. 4A is a schematic side view illustrating the first holding section of the end effector of the treatment device of the treatment system according to the first embodiment, and illustrating a state in which the inner surface of the cover is spaced apart from the back surface of the treatment portion.
Figure 4B:
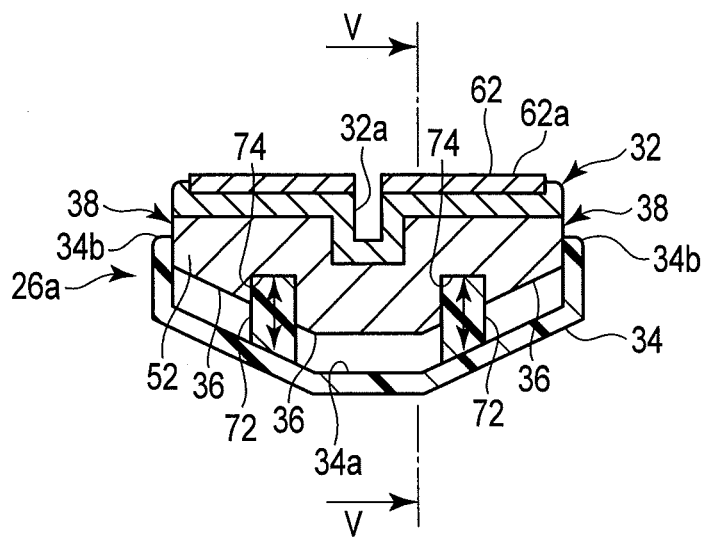
FIG. 4B is a schematic transverse cross-sectional view, taken along line 4B-4B in FIG. 4A, illustrating the first holding section of the end effector of the treatment device of the treatment system according to the first embodiment.
Figure 5:
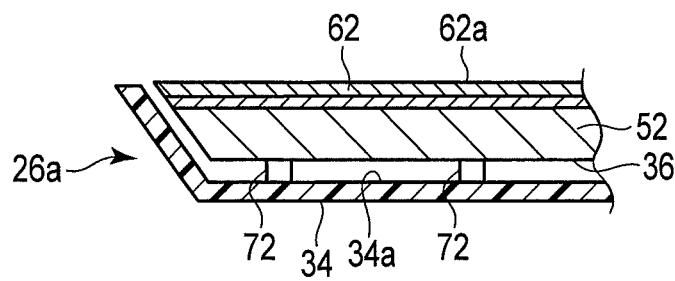
FIG. 5 is a schematic longitudinal cross-sectional view, taken along line V-V in FIG. 4B, illustrating the first holding section of the end effector of the treatment device of the treatment system according to the first embodiment.

The first cover 34 covers the back surface 36 of the first jaw 52, that is, the first treatment portion 32. The adjustor 72 is disposed between the back surface 36 of the first treatment portion 32 and the first cover 34, the adjustment portion 72 adjusting the air layer region (thermal insulation layer region) such that the air layer region can be increased or decreased. Specifically, the adjuster 72 can increase or decrease the thickness of the air layer. As illustrated in FIG. 3B, FIG. 4B and FIG. 5, it is preferable that a plurality of adjusters 72 are provided, and at least three adjusters 72 are provided in this embodiment. The adjuster 72 lies between the back surface 36 of the treatment portion 32 and the inner surface 34a of the cover 34, and couples these. The adjuster 72 increases the distance between the back surface 36 of the first treatment portion 32 and the inner surface 34a of the cover 34 in accordance with a rise in temperature of the back surface 36 of the first treatment portion 32, and increases the air layer region between the back surface 36 of the first treatment portion 32 and the inner surface 34a of the cover 34. The adjuster 72 decreases the distance between the back surface 36 of the first treatment portion 32 and the inner surface 34a of the first cover 34 in accordance with a fall in temperature of the back surface 36, and decreases the air layer region. It is preferable that the air layer region does not exist if the inner surface 34a of the cover 34 is put in contact with the back surface 36 of the first treatment portion 32.

The first energy output portion 62 has the holding surface 62a which comes in contact with, and holds, the living body tissue of the treatment target. The first jaw 52 holds the first energy output portion 62. If energy is supplied to the first energy output portion 62, the living body tissue of the treatment target is not only heated, but part of the heat is conveyed toward the back surface 36 of the first jaw 52 via the first jaw 52.

The adjuster 72 is disposed between the treatment portion 32 and cover 34. A recess portion 74, in which the adjuster 72 is disposed, is formed in the back surface 36 of the first jaw 52. Although depending on the shape and size of the adjuster 72, the inner surface 34a of the cover 34 can come in contact with the back surface 36 of the jaw 52 at normal temperature (e.g. room temperature in an operating room).

The adjuster 72 according to this embodiment is formed by using a shape memory alloy which expands if heated up to a temperature exceeding, for example, a predetermined temperature, and contracts if cooled, or a polymer resin having, for example, heat resistance. When the shape memory alloy is used for the adjuster 72, the adjuster 72 is formed, for example, in a coil shape. When the polymer resin is used for the adjuster 72, the adjuster 72 is formed, for example, in a substantially cylindrical shape.

In addition, the adjuster 72 can perform adjustment in a manner to increase the distance between the treatment portion 32 and the cover 34 in accordance with a rise in temperature of the first back surface 36 of the first treatment portion 32 and to increase the air layer region between the treatment portion 32 and the cover 34, and in a manner to decrease the distance between the treatment portion 32 and the cover 34 in accordance with a fall in temperature of the back surface 36 and to decrease the air layer region.

Specifically, the adjuster 72 of this embodiment is a thermal deformation body which thermally deforms in a manner to increase the distance between the treatment portion 32 and the cover 34 in accordance with a rise in temperature of the first back surface 36 of the first treatment portion 32 and to increase the air layer region between the treatment portion 32 and the cover 34, and in a manner to decrease the distance between the treatment portion 32 and the cover 34 in accordance with a fall in temperature of the back surface 36 and to decrease the air layer region. The distance between the jaw 52 and cover 34 is varied in accordance with the temperature of the back surface 36 of the jaw 52 by the adjuster (thermal deformation body) 72 which is deformed in accordance with the heat that is conveyed via the jaw 52.

The first jaw 52 or the first energy output portion 62 includes a side surface 38 of the treatment portion 32. Specifically, the treatment portion 32 includes the holding surface 62a which is abutted on the living body tissue of the treatment target, the back surface 36 opposed to the holding surface 62a, and the side surfaces 38 between the holding surface 62a and back surface 36. The side surfaces 38 may be formed by the first jaw 52 and first energy output portion 62. In this embodiment, a description is given on the assumption that the first jaw 52 includes the side surface 38. The cover 34 covers at least a part of the side surface 38 of the treatment portion 32, regardless of a variation in shape of the adjuster 72.

In the present embodiment, for the purpose of simple description, it is assumed that when the back surface 36 of the treatment portion 32 is at normal temperatures, the inner surface 34a of the cover 34 abuts on the back surface 36 of the treatment portion 32, and the first holding surface 62a is flush with the edge portion 34b of the first cover 34. As described above, the edge portion 34b of the first cover 34 can approach, and move away from, the holding surface 62a of the energy output portion 62. When the edge portion 34b approaches the holding surface 62a, the inner surface 34a of the cover 34 approaches the back surface 36 of the treatment portion 32. When the edge portion 34b moves away from the holding surface 62a, the inner surface 34a of the cover 34 moves away from the back surface 36 of the treatment portion 32.

An indicator 38a and scale marks 38b, which indicate the positional relationship between the edge portion 34b of the first cover 34 and the first holding surface 62a, are provided on the side surface 38. It is preferable that the indicator 38a and scale marks 38b are provided not only on the left side surface, as illustrated in FIG. 4A, but also on the right side surface. The indicator 38a and scale marks 38b can be observed by an observation optical system 92 (to be described later). The indicator 38a and scale marks 38b on the side surface 38 function as a display element which indicates the temperature state of the back surface 36 of the treatment portion 32, based on the positional relationship between the holding surface 62a of the treatment portion 32 and the edge portion 34b of the cover 34.

The indicator 38a is provided, for example, by color coding on the side surface 38, and can be used as a temperature display of the back surface 36, which corresponds to the movement of the edge portion 34b of the first cover 34 relative to the first holding surface 62a. The scale marks 38b can be used as a display indicating, for example, the amount of movement of the edge portion 34b of the first cover 34 relative to the first holding surface 62a.

The scale marks 38b on the side surface 38 can be used as a temperature display of the back surface 36 of the treatment portion 32, if the amount of movement of the edge portion 34b of the cover 34 relative to the holding surface 62a, which is based on the amount of deformation of the adjuster 72 corresponding to the temperature of the back surface 36 of the treatment portion 32, was measured in advance. Specifically, the scale marks 38b can also be used as a temperature display which is complementary to the indicator 38a.

The energy source 14 according to this embodiment includes a controller 82, an energy output circuit 84, a setting input unit 86, and a speaker (sound generator) 88. A display unit 90, such as a monitor, is connected to the energy source 14. Information (for example, an output amount, an output time, etc. to the energy output portions 62, 64 from the energy output circuit 84), which was input by the setting input unit 86, is displayed on the display unit 90. The speaker 88 is controlled so as to generate an alarm sound, for example, when abnormality occurred in the treatment system 10.

In addition, it is preferable that the treatment device 12 according to this embodiment is used together with an observation optical system 92 such as an endoscope. The observation optical system 92 is connected to the controller 82 of the energy source 14 via a camera control unit (CCU) 94. An image, which was captured by the observation optical system 92, can be displayed on the display unit 90.

In the meantime, as illustrated in FIG. 3B and FIG. 4B, it is preferable that the first treatment portion 32 includes a guide groove 32a for a treatment ancillary instrument 102 shown in FIG. 1B. In this embodiment, a cutter shown in FIG. 1B is described as the treatment ancillary instrument 102.

As illustrated in FIG. 1A, the handle 22 includes a movement lever 22b for moving, in the axial direction, the cutter serving as the treatment ancillary instrument 102 shown in FIG. 1B. If the movement lever 22b is operated, a blade 102a that is a distal end of the treatment ancillary instrument 102 can move along the guide groove 32a. Although not illustrated, it is preferable that a similar guide groove is formed in the second treatment portion 42, and the treatment ancillary instrument 102 is guided by the first and second treatment portions 32 and 42 to assist in treatment. Incidentally, the guide groove 32a and treatment ancillary instrument 102 may not necessarily be provided.

Next, the operation of the treatment system 10 according to this embodiment is described.

For example, when the end effector 26 is guided into a body cavity, in which a living body tissue of a treatment target is present, from the outside of the body cavity, the end effector 26 is passed through a narrow cavity. Thus, in order to make the end effector 26 as small as possible, it is preferable that the treatment portion 32 and cover 34 abut on each other.

In the meantime, when a living body tissue is treated, the observation optical system 92, such as an endoscope, is guided into the body cavity. Then, an observation image of the observation optical system 92 is displayed on the display unit 90.

The end effector 26 in this state is made to face the living body tissue of the treatment target, the operation lever 22a of the handle 22 is operated, the first and second treatment portions 32 and 42 are opened and closed, and the living body tissue of the treatment target is held between the first and second holding surfaces 62a and 64a. In this state, the pedal 16a of the foot switch 16 is operated, and energy is applied from the energy output portions 62 and 64 to the living body tissue of the treatment target.

At this time, heat is generated by the energy output portions 62 and 64. Hereinafter, since the operations of the first and second holding sections 26a and 26b are identical, the operation of only the first holding section 26a is described, and a description of the operation of the second holding section 26b is omitted.

The heat generated by the energy output portion 62 is transferred to the living body tissue of the treatment target via the holding surface 62a, and the living body tissue of the treatment target is heated and treated. The temperature of the holding surface 62a at this time is controlled so as to rise from normal temperatures to, for example, about 200° C. In the meantime, when the back surface 36 of the treatment portion 32 is at normal temperatures, the indicator 38a and scale marks 38b on the side surface 38, that is, the display element, cannot be observed by the observation optical system 92 due to the edge portion 34b of the cover 34.

The heat generated by the energy output portion 62 is transferred not only to the living body tissue of the treatment target via the holding surface 62a, but also to the jaw 52 of, e.g. stainless steel. Thus, part of the heat generated by the energy output portion 62 is transferred to the back surface 36 of the jaw 52, that is, the back surface 36 of the treatment portion 32, through the jaw 52. This heat is transferred from the back surface 36 of the treatment portion 32 to the adjuster 72.

When the back surface 36 of the treatment portion 32, that is, the adjuster 72, is at normal temperatures, the adjuster 72 does not deform, and the state is maintained in which the inner surface 34a of the cover 34 abuts on the back surface 36 of the jaw 52. For example, when the holding surface 62a was heated up to 200° C., the heat at a temperature between a temperature exceeding the normal temperatures and 200° C. is conveyed to the back surface 36 of the jaw 52. Thus, with the heat being conveyed to the back surface 36 of the jaw 52, that is, to the adjuster 72, the temperature rises from normal temperatures. Then, due to the effect of the heat, the adjuster 72 expands in the axial direction and radial direction.

If the adjuster 72 expands in the axial direction and radial direction in this manner, the inner surface 34a of the cover 34 moves away from the back surface 36 of the jaw 52. Accordingly, an air layer forms between the back surface 36 of the jaw 52 and the inner surface 34a of the cover 34. If the adjuster 72 expands in the axial direction in accordance with a temperature rise, the air layer gradually becomes larger. However, if the amount of expansion of the adjuster 72, which corresponds to the temperature rise, increases to a predetermined amount, this state is maintained.

Since the material with adiathermancy is used for the cover 34, the thermal effect on the living body tissue around the living body tissue of the treatment target can be suppressed to be lower than in the state in which the cover 34 abuts on the back surface 36 of the treatment portion 32.

In the meantime, as the temperature of the back surface 36 of the treatment portion 32 rises from normal temperatures to such a temperature as to treat the living body tissue and the adjuster 72 is thermally deformed, the edge portion 34b of the cover 34 gradually moves away from the holding surface 62a, and the scale marks 38b on the side surface 38 are observed by the observation optical system 92. Thus, the display unit 90 displays an image which was observed by the observation optical system 92, and enables the user to recognize the increase and decrease of the air layer region between the treatment portion 32 and the cover 34. Therefore, if the relationship between the temperatures of the back surface 36 and the indicator 38a and scale marks 38b on the side surface 38 is checked in advance, the temperature of the back surface 36 can be estimated.

If the supply of energy is stopped, the heat transfer amount from the energy output portion 62 to the jaw 52 gradually decreases. Thus, the heat transfer amount from the energy output portion 62 to the adjuster 72 via the jaw 52, that is, the heat transfer amount from the treatment portion 32 to the adjuster 72, gradually decreases, and the amount of expansion of the adjuster 72 in the axial direction gradually decreases. In the case of drawing out the end effector 26 from the body cavity, when the heat at a temperature exceeding normal temperatures is being transferred to the back surface 36 of the jaw 52, the inner surface 34a of the cover 34 is spaced apart from the back surface 36 of the jaw 52. Thus, the thermal effect on the peripheral tissue can be prevented as much as possible.

Then, the inner surface 34a of the cover 34, which was spaced apart from the back surface 36 of the jaw 52, gradually approaches the back surface 36 of the jaw 52. If the temperature of heat transferred to the adjuster 72 falls to normal temperatures, the inner surface 34a of the cover 34 abuts on the back surface 36 of the jaw 52.

As has been described above, according to this embodiment, the following can be said.

When the back surface 36 of the first treatment portion 32 is at normal temperatures, the inner surface 34a of the first cover 34 is in contact with, or is closest to, the back surface 36 of the first jaw 52 of the first treatment portion 32. Thus, when the end effector 26 is made to face the living body tissue of the treatment target, the end effect 26 can easily be guided through a narrow cavity.

If heat is transferred from the energy output portion 62 to the first jaw 52 by the energy output at the energy output portion 62, and the temperature of the adjuster 72 provided at the back surface 36 of the first jaw 52 rises, the back surface 36 of the first jaw 52 and the inner surface 34a of the first cover 34 can automatically be spaced apart by the operation of the adjuster 72. Thus, the thermal effect on the living body tissue around the living body tissue of the treatment target can be suppressed to be lower than in the state in which the cover 34 abuts on the back surface 36 of the treatment portion 32.

Therefore, according to this embodiment, there can be provided the treatment device 12 which, when moved in a tract, can easily be moved with a smallest possible distance, that is a smallest possible thickness of the heat insulation layer (air layer), between the treatment portion 32 and cover 34, and which can form the thermal insulation layer (air layer) between the treatment portion 32 and cover 34, the thickness of the thermal insulation layer being adjustable in accordance with the heat conveyed to the treatment portion 32 by the energy output.

The indicator 38*a* and/or scale marks 38*b* are formed on the side surface 38 of the treatment portion 32, and the indicator 38*a* and/or scale marks 38*b* are observed on the display unit 90 through the observation optical system 92. Thereby, the temperature of the back surface 36 of the treatment portion 32 can easily be recognized. Specifically, the temperature of the back surface 36 of the treatment portion 32 can be visually presented to the user. In addition, it is easy to recognize simply the fact that the cover 34 is spaced apart from the back surface 36 of the treatment portion 32 due to a temperature rise.

In the meantime, in the present embodiment, the description has been given on the assumption that when the back surface 36 of the treatment portion 32 is at normal temperatures, the inner surface 34*a* of the cover 34 abuts on the back surface 36 of the treatment portion 32, and the first holding surface 62*a* is flush with the edge portion 34*b* of the first cover 34. Although the inner surface 34*a* of the cover 34 becomes closest to the back surface 36 of the treatment portion 32 when the back surface 36 of the treatment portion 32 is at normal temperatures, it is also preferable that a space is created at this time. In addition, it is preferable that when the back surface 36 of the treatment portion 32 is at normal temperatures, the edge portion 34*b* of the cover 34 is disposed in such a manner to expose a part of the side surface at a position on the side closer to the holding surface 62*a*.

Figure 6:
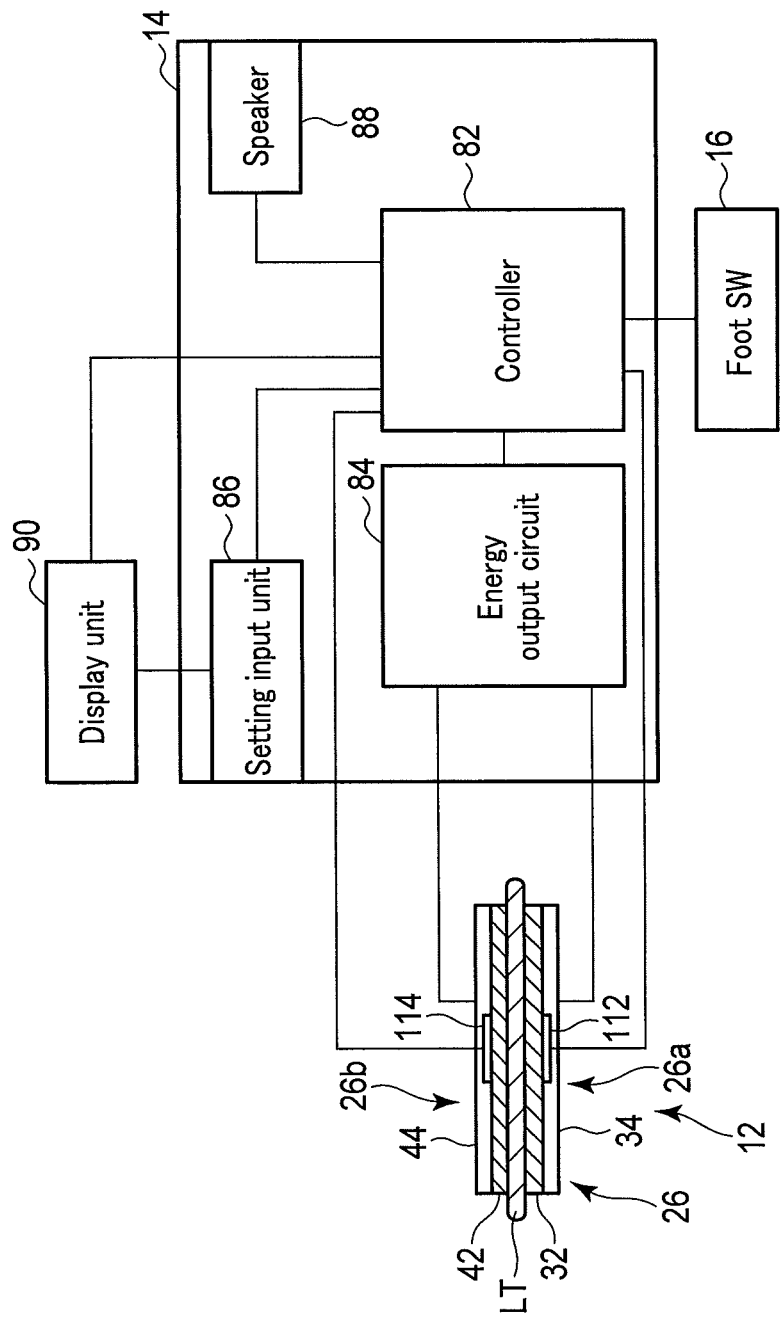
FIG. 6 is a schematic block diagram of a treatment system according to a second embodiment.

Next, a second embodiment is described with reference to FIG. 6 to FIG. 7B. This embodiment is a modification of the first embodiment, and the same members, or the members having the same functions, as the members described in the first embodiment are denoted by like reference numerals as much as possible, and a detailed description thereof is omitted.

In this embodiment, a description is given of a modification of a connection state between the first jaw 52 and cover 34.

Distance sensors 112 and 114 are disposed between the back surface 36 of the first treatment portion 32 and the inner surface 34*a* of the first cover 34 and between the back surface of the second treatment portion 42 and the inner surface of the second cover 44, respectively, and the distance sensors 112 and 114 can measure the distances therebetween, respectively. These distance sensors 112 and 114 are controlled by the controller 82. For example, the distance sensor 112 may be disposed on the back surface 36 of the first treatment portion 32, or may be disposed on the inner surface 34*a* of the first cover 34, or may be disposed on both. In addition, the distance sensor 112 functions as a detection element which detects an increase and a decrease of the air layer region between the treatment portion 32 and the cover 34.

The adjuster 72 adjusts the distance between the back surface 36 of the treatment portion 32 and the cover 34 in accordance with the temperature of heat transferred to the back surface 36 of the jaw 52. By checking in advance the relationship between the distance between the back surface 36 of the treatment portion 32 and the inner surface 34*a* of the first cover 34, on one hand, and the temperature of the back surface 36 of the treatment portion 32, on the other hand, the temperature of the back surface 36 of the treatment portion 32 can be displayed on the display unit 90 and notified to the user, even without observing the indicator 38*a* and scale marks 38*b* by the observation optical system 92 as described in the first embodiment.

In this manner, by measuring the distance by the distance sensor 112, the temperature of the back surface 36 of the first treatment portion 32 can be estimated.

Needless to say, it is preferable to add the indicator 38*a* and scale marks 38*b* to the side surface 38.

The speaker 88, which generates a sound, such as a beep sound, when the distance measured by the distance sensor 112 begins to increase (the air layer region begins to increase), is connected to the controller 82. Thus, by the generation of sound, it is possible to inform the user that the back surface 36 of the first jaw 52 is at a predetermined temperature or above. By varying the sound that is generated, it is possible to inform the user that the distance measured by the distance sensor 112 is kept in an operation state relative to a reference state, and that the operation is being performed. Besides, by detecting that the distance measured by the distance sensor 112 is increasing (the air layer region is increasing) or decreasing (the air layer region is decreasing), it is possible to vary the sound at a time when the temperature is rising and the sound at a time when the temperature is falling.

The display unit (monitor) 90 is connected to the controller 82. The display unit 90 displays information of a patient and the setting state of the device. In addition, the display unit 90 according to this embodiment can display that the cover 34 abuts on the treatment portion 32 or is spaced apart from the treatment portion 32, based on the distance measured by the distance sensor 112, when the temperature of the first jaw 52 rises, and can display the distance of spacing when the cover 34 is spaced apart from the treatment portion 32.

Accordingly, the speaker 88 and/or display unit 90 functions as a recognition unit, and makes the user recognize that the distance sensor (detection element) 112 detects the air layer region increasing, the air layer region decreasing, or the air layer region being kept in a fixed state. In particular, when the air layer region has begun to increase, it is indicated that the temperature of the back surface 36 of the treatment portion 32 has begun to rise. Thus, it is possible to make the user easily recognize, by the speaker 88 and/or display unit 90, that the cover 34 has begun to move relative to the treatment portion 32.

In addition, it is preferable to use a pressure sensor (detection element) together with the distance sensor or in place of the distance sensor. Specifically, for example, a pressure sensor may be used in place of the distance sensor 112, 114.

When the pressure sensor is used, the highest pressure is measured in the state in which the inner surface 34*a* of the first cover 34 abuts on the back surface 36 of the first jaw 52. In accordance with a rise in temperature of the back surface 36 of the first jaw 52, the inner surface 34*a* of the first cover 34 is moving away from the back surface 36 of the first jaw 52, and accordingly the pressure becomes lower. By checking in advance the relationship between the pressure between the back surface 36 of the treatment portion 32 and the inner surface 34a of the first cover 34, on one hand, and the temperature of the back surface 36 of the treatment portion 32, on the other hand, the state of the temperature can be displayed on the display unit 90 and thereby notified to the user, even without observing the indicator 38a and scale marks 38b by the observation optical system 92 as described in the first embodiment.

In this manner, by measuring the pressure of the inner surface 34a of the first cover 34 relative to the back surface 36 of the first jaw 52 by the pressure sensor, the temperature of the back surface 36 of the first treatment portion 32 can be estimated.

In addition, it is preferable to use a bimetal switch (detection element) together with the distance sensor or pressure sensor, or in place of the distance sensor or pressure sensor, the bimetal switch being configured such that a first metal is disposed on the back surface 36 of the first jaw 52 and a second metal, which is different from the first metal, is disposed on the inner surface 34a of the first cover 34.

Next, a third embodiment is described with reference to FIG. 8 to FIG. 9B. This embodiment is a modification of the first and second embodiments, and the same members, or the members having the same functions, as the members described in the first and second embodiments are denoted by like reference numerals as much as possible, and a detailed description thereof is omitted.

As illustrated in FIG. 8, a temperature sensor (temperature measuring unit) 132, 134 for measuring the temperature of the back surface 36, and an actuator 142, 144 functioning as an adjuster for moving the cover 34, 44 relative to the jaw 52, 54 in accordance with temperatures, are disposed on the back surface 36 of the first jaw 52, that is, on the back surface 36 of the treatment portion 32. Specifically, the adjuster 72 according to this embodiment includes the actuator 142, 144 for adjusting the distance between the treatment portion 32, 42 and cover 34, 44, based on a measurement result of the temperature measured by the temperature sensor 132, 134. The actuator 142, 144 is connected to an actuator driving circuit 146 which is disposed in the energy source 14. The temperature sensor 132, 134 and actuator 142, 144 are connected to the controller 82. The actuator driving circuit 146 drives the actuator 142, 144 so as to adjust the distance between the treatment portion 32 and cover 34, based on the measurement result measured by the temperature sensor 132, 134.

Figure 9A:
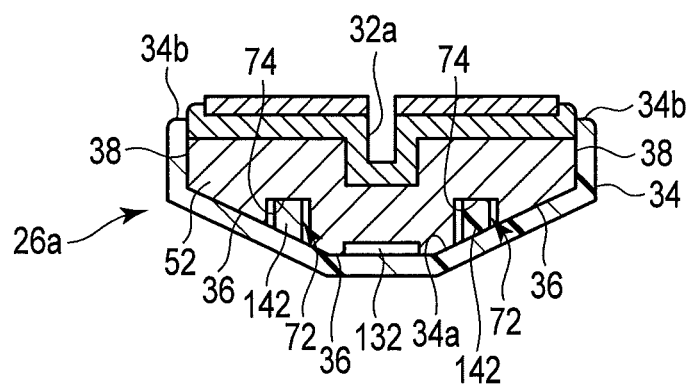
FIG. 9A is a schematic transverse cross-sectional view illustrating a first holding section of an end effector of a treatment device of the treatment system according to the third embodiment, and illustrating a state in which an inner surface of a cover abuts on a back surface of a treatment portion.
Figure 9B:
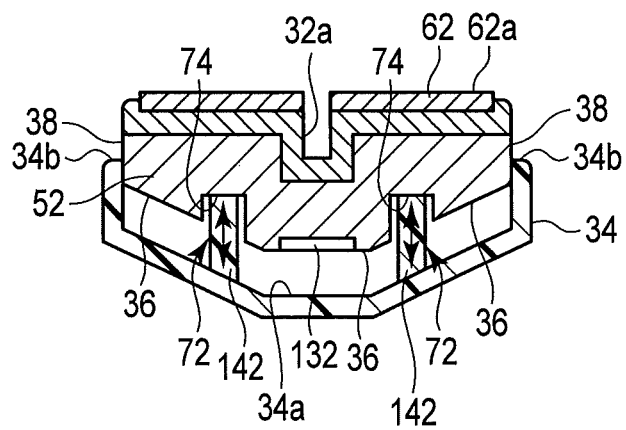
FIG. 9B is a schematic transverse cross-sectional view illustrating the first holding section of the end effector of the treatment device of the treatment system according to the third embodiment, and illustrating a state in which the inner surface of the cover is spaced apart from the back surface of the treatment portion.

As illustrated in FIG. 9A and FIG. 9B, the temperature sensor 132 is disposed on the back surface 36 of the treatment portion 32, and actuators 142 are disposed between the back surface 36 of the treatment portion 32 and the inner surface 34a of the cover 34. The actuators 142 are operated based on the temperature measured by the temperature sensor 132. Thus, for example, when the temperatures measured by the temperature sensor 132 are room temperatures in an operating room in a range of, e.g. about 10° C. to 40° C., the actuator 142 is not operated. If the temperature rises to a level higher than 40° C., the actuators 142 are operated in accordance with the temperature so as to space the inner surface 34a of the cover 34 apart from the back surface 36 of the first jaw 52.

Incidentally, it is preferable that a maximum spacing distance of the inner surface 34a of the first cover 34 from the back surface 36 of the first jaw 52 is set for the actuators 142. In this case, the maximum spacing distance does not vary, even if the temperature sensor 132 detects temperatures higher than a predetermined temperature.

The speaker 88, which generates a sound, such as a beep sound, when the actuators 142 begin to operate, is connected to the controller 82. Thus, by the generation of sound, it is possible to inform the user that the back surface 36 of the first jaw 52 is at a predetermined temperature or above. By varying the sound that is generated, it is possible to inform the user that the actuators 142 are kept in an operation state relative to a reference state, and that the operation is being performed. Besides, it is possible to vary the sound at a time when the temperature is rising and the sound at a time when the temperature is falling.

The display unit (monitor) 90 is connected to the controller 82. The display unit 90 displays information of a patient and the setting state of the device. In addition, the display unit 90 according to this embodiment can display that the temperature of the first jaw 52 rises, and the actuators 142 are kept in an operation state relative to a reference state, or that the actuators 142 are operating.

In the meantime, as described in the first embodiment, it is preferable that the indicator 38a and/or scale marks 38b are added to the side surface 38. The actuators 142 are operated in accordance with the temperature measured by the temperature sensor 132. Thus, for example, by confirming the indicator 38a and/or scale marks 38b by using the observation optical system 92 such as an endoscope, the user can visually confirm the temperature.

Next, a fourth embodiment is described with reference to FIG. 10A. This embodiment is a modification of the first to third embodiments, and the same members, or the members having the same functions, as the members described in the first to third embodiments are denoted by like reference numerals as much as possible, and a detailed description thereof is omitted. In this embodiment, a description is given of a modification of the connection state between the first jaw 52 and cover 34.

As illustrated in FIG. 10A, a distal end of the first jaw 52 and a distal end of the cover 34 are rotatably supported by a pin 152 functioning as a coupling unit. The pin (coupling unit) 152 is disposed at the edge portion 34b of the cover 34 or in a vicinity thereof. In this case, too, the number of adjusters 72 may be one or plural, but it is preferable that the number of adjusters 72 is plural.

In the meantime, a modification of the fourth embodiment is described with reference to FIG. 10B.

As illustrated in FIG. 10B, on the back surface 36 side of the first jaw 52, a plurality of recess portions 162, which are formed in recessed shapes relative to the back surface, are formed. Projection portions 164, which can be inserted in and drawn out from the recess portions 162, are formed on the inner surface 34a of the cover 34. The projection portions 164 of the cover 34 are slidably disposed in the recess portions 162 of the first jaw 52. By the deformation of the adjuster 72 or the operation of the actuator 142, the cover 34 can be moved closer to or away from the first jaw 52.

Next, a fifth embodiment is described with reference to FIG. 11A to FIG. 11C. This embodiment is a modification of the first to fourth embodiments, and the same members, or the members having the same functions, as the members described in the first to fourth embodiments are denoted by like reference numerals as much as possible, and a detailed description thereof is omitted. In this embodiment, a description is given of an example in which a cutter unit 172, which differs in structure from the treatment ancillary instrument 102 shown in FIG. 1B, is used.

As illustrated -in FIG. 11A to FIG. 11C, the cutter unit 172 is provided in the first treatment portion 32 and second treatment portion 42. The cutter unit 172 includes a circular cylindrical body 174, a curved-surface body 176 which constitutes a part of a circular cylinder, and a blade 178 which is formed on an edge portion of the curved-surface body 176. The blade 178 includes a distal-end blade 178a, a proximal-end blade 178b, and a central blade 178c. The central blade 178c is formed continuous with the distal-end blade 178a and the proximal-end blade 178b.

The first treatment portion 32 includes a first guide groove 32b having a curved-surface shape, which guides the curved-surface body 176 and blade 178 of the cutter unit 172. The second treatment portion 42 includes a second guide groove 42b having a curved-surface shape, which guides the curved-surface body 176 and blade 178 of the cutter unit 172.

The circular cylindrical body 174 is rotatable about an axis C1 (see FIG. 11B) which is, preferably, parallel to the center axis C, unlike the center axis C in FIG. 1A. If the circular cylindrical body 174 rotates about the axis C1, the blade 178 is fed out from inside the guide groove 32b of the first jaw 52 into the guide groove 42b of the second jaw 54.

As illustrated in FIG. 11C, when the blade 178 is projected from the guide groove 32b of the first treatment portion 32, the central blade 178c firstly project to the outside, and thereafter the distal-end blade 178a and proximal-end blade 178b project. Then, as illustrated in FIG. 11A, the blade 178 is accommodated in the guide groove 42b of the second jaw 54.

In this embodiment, the blade 178 of the cutter unit 172 is configured such that the central part is formed in a projecting shape relative to the distal end and proximal end. Thus, the central part of the blade 178 firstly projects out from the holding surface 62a of the energy output portion 62, and the living body tissue, to which thermal energy was applied from the distal end toward the proximal end, can be cut from the center toward the ends.

Although not illustrated, it is preferable that the covers 34 and 44 are disposed on the treatment portions 32 and 42 shown in FIG. 11A via the adjusters 72, respectively.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device which is capable of treating a living body tissue by using energy, the treatment device comprising:
   a treatment portion including an abutment surface which is configured to abut on the living body tissue, and a back surface opposed to the abutment surface, the treatment portion being configured to apply energy to the living body tissue via the abutment surface, and being configured to transfer heat toward the back surface in accordance with the application of the energy;
   a cover covering the back surface of the treatment portion; and
   an adjuster disposed between the treatment portion and the cover, the adjuster being configured to vary a distance between the treatment portion and the cover and adjust an air layer region between the treatment portion and the cover, wherein:
   the adjuster is configured to thermally deform in a manner to increase the distance between the treatment portion and the cover in accordance with the rise in temperature of the back surface of the treatment portion due to the application of the energy, and to increase the air layer region between the treatment portion and the cover, and in a manner to decrease the distance between the treatment portion and the cover in accordance with the fall in temperature of the back surface, and to decrease the air layer region.

2. The treatment device according to claim 1, wherein the cover is abutted on the back surface of the treatment portion in accordance with a fall in temperature of the back surface of the treatment portion.

3. The treatment device according to claim 1, wherein the cover has heat resistance property, and thermal insulation property to prevent a thermal effect on a living body tissue around the living body tissue.

4. The treatment device according to claim 1, further comprising an operation portion configured to operate the treatment portion, wherein the treatment portion includes a pair of jaws which are operated by the operation portion and are openable/closable relative to each other.

5. The treatment device according to claim 1, wherein the adjuster is configured to couple the treatment portion and the cover.

6. A treatment device which is capable of treating a living body tissue by using energy, the treatment device comprising:
   a treatment portion including an abutment surface which is configured to abut on the living body tissue, and a back surface opposed to the abutment surface, the treatment portion being configured to apply energy to the living body tissue via the abutment surface, and being configured to transfer heat toward the back surface in accordance with the application of the energy;
   a cover covering the back surface of the treatment portion; and
   an adjuster disposed between the treatment portion and the cover, the adjuster being configured to vary a distance between the treatment portion and the cover and adjust an air layer region between the treatment portion and the cover, wherein:
   the treatment portion includes a side surface between the abutment surface and the back surface, the cover includes an edge portion which covers at least a part of the side surface of the treatment portion, and is capable of moving closer to and away from the abutment surface, and the side surface of the treatment portion includes a display element configured to indicate a temperature state of the back surface of the treatment portion, based on a positional relationship between the abutment surface of the treatment portion and the edge portion of the cover.

7. A treatment system comprising:
   the treatment device according to claim 6;
   an observation optical system configured to capture an image of the display element; and
   a display unit configured to display the image observed by the observation optical system, and to cause a user to recognize an increase and a decrease of the air layer region between the treatment portion and the cover.

* * * * *